United States Patent [19]
Söderlund et al.

[11] Patent Number: 5,989,817
[45] Date of Patent: *Nov. 23, 1999

[54] TARGET NUCLEIC ACID AND CAPTURE METHOD

[76] Inventors: Hans Erik Söderlund, Salonkitie 19, 02940 Espoo; Arja Marjatta Weckman, Tallberqin puistotie 6 A 5, 00200 Helsinki, both of Finland

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/917,404

[22] Filed: Aug. 25, 1997

Related U.S. Application Data

[60] Continuation of application No. 08/500,695, Jul. 11, 1995, abandoned, which is a division of application No. 07/610,470, Nov. 7, 1990, Pat. No. 5,476,769, which is a continuation of application No. 07/024,604, Mar. 11, 1987, abandoned.

[51] Int. Cl.$^6$ ............... C12Q 1/68; C12P 19/34; C07H 21/04; C07H 21/02
[52] U.S. Cl. ............... 435/6; 435/91.1; 435/91.2; 536/23.1; 536/24.3; 536/24.33; 935/77; 935/78
[58] Field of Search ............... 435/6, 5, 91.1, 435/91.2; 536/23.1, 24.3, 24.33; 935/77, 78

[56] References Cited

U.S. PATENT DOCUMENTS

| | | | |
|---|---|---|---|
| 4,581,333 | 4/1986 | Kourilsky et al. | 435/6 |
| 4,605,735 | 8/1986 | Miyoshi et al. | 536/27 |
| 4,683,202 | 7/1987 | Mullis | 435/91 |
| 4,851,331 | 7/1989 | Vary et al. | 435/6 |

*Primary Examiner*—Stephanie Zitomer
*Attorney, Agent, or Firm*—Baker & Botts; Richard S. Clark

[57] ABSTRACT

The present invention provides a rapid and sensitive method for assaying nucleic acids by means of hybridization techniques, wherein the detector probes are modified primers being incorporated into copies of the target nucleic acid before the hybridization reaction and a reagent combination as well as a kit therefor. The invention also provides a method for assaying nucleic acids by means of hybridization techniques, wherein the capturing probes are modified primers being incorporated into copies of the target nucleic acids before the hybridization reaction.

9 Claims, 2 Drawing Sheets

TARGET NUCLEIC ACID AND CAPTURE METHOD

This application is a continuation of application Ser. No. 08/500,695, filed on Jul. 11, 1995, now abandoned, which is a division of application Ser. No. 07/610,470, now U.S. Pat. No. 5,476,769, filed on Nov. 7, 1990, which is a continuation of application Ser. No. 07/024,604, filed on Mar. 11, 1987, abandoned.

TECHNICAL FIELD

The present invention relates to a rapid and sensitive method for assaying nucleic acids by means of hybridization techniques, wherein the detector probes are modified primers being incorporated into copies of the target nucleic acid before the hybridization reaction and a reagent combination as well as a kit therefore.

Moreover, the invention relates to a method for assaying nucleic acids by means of hybridization techniques, wherein the capturing probes are modified primers being incorporated into copies of the target nucleic acids before the hybridization reaction and a reagent combination as well as a kit therefore.

BACKGROUND OF INVENTION

In hybridization reactions a labelled oligo- or polynucleotide, i.e. the probe is allowed to base-pair with the nucleic acid target. Various hybridization methods have been used for the detection of nucleic acids. In direct hybridization methods the specimen is either in solution or fixed to a solid carrier. The nucleic acid which is to be identified is demonstrated using one labelled probe.

In U.S. Pat. No. 4,486,539 a sandwich hybridization method has been described. In this method two separate probes are used, one being a detector probe labelled and used for detection and the other being a capturing probe immobilized to a solid carrier for the separation of the target nucleic acid from the reaction mixture.

The method of hybridization in solution is described in British Patent Publication No. 2 169 403. Two different probes both being in the same solution phase are used in this method. The detector probe is labelled with a detectable label and to the capturing probe a moiety having affinity for another component is attached. After the hybridization the hybrid formed between the capturing probe, target nucleic acid and the detector probe, may be separated from the hybridization solution by the aid of the other moiety of the affinity pair.

The enzyme catalyzed polymerization of DNA where the nucleotide sequence of a previously existing nucleic acid strand, i.e. the template is accurately copied into its complementary strand, is well-known in the art and has been described e.g. in Kornberg, DNA replication, W. H. Freeman & Co, San Francisco, pp. 221–225 and 670–679, 1980 and Maniatis et al., Molecular Cloning, A Laboratory Manual, Cold Spring Harbor Laboratory, p. 122, 1982. This biological multiplication is used in hybridization assays in which the microbe to be detected is cultivated and hence its DNA enriched prior to the test and is described e.g. in Woo, Methods Enzymol. 68, p. 389, 1979 and in U.S. Pat. No. 4,358,535. Specific DNA sequences can also be amplified within living cells e.g. by the use of suitable drugs as described by Clewell and Helinski in J. Bacteriol. 110, p. 1135, 1972 and in European Patent Application No. 55 742. A more specific DNA-enrichment is described in in the European Patent Application No. 175 689 in which the target is linked to a plasmid replicon and introduced into a suitable cell. Yet another method is described in the European Patent Application No. 201 184, in which the primer dependence of DNA synthesis is utilized to create an in vitro reaction for the amplification of the target DNA. In the European Patent Application No. 200 362 a method for detecting amplified genes is suggested.

SUMMARY OF INVENTION

In the hybridization method of the present invention either the detector probes or the capturing probes act as modified primers being incorporated into the copies of the target nucleic acid in a template dependent polymerization process before the hybridization reaction.

In the method of the invention at least one primer is needed and the primers are always modified. If the detector probes act as primers in the polymerization reaction, the primers are provided with at least one suitable, detectable label or at least one specific site whereto at least one suitable, detectable label can be attached.

Alternatively the capturing probes can be used as primers in the polymerization reaction, in which case the primers are provided with at least one suitable moiety of an affinity pair or at least one site whereto at least one suitable moiety of an affinity pair can be attached.

The invention also discloses a reagent combination and a kit comprising in packaged form a multicontainer unit comprising the reagent combination needed for the performance of the test.

By using the detector or capturing probes as primers in a polymerization reaction it is possible to increase the sensitivity of the hybridization reaction by several orders of magnitude compared with methods measuring the target directly. Furthermore, the invention provides a convenient method to perform the hybridization reaction in solution so that the hybrids are easily and rapidly separated from the hybridization solution after the hybridization reaction.

The method of the invention is convenient for diagnosting certain diseases, which are very difficult to diagnose with conventional methods. Thus the method is especially useful for the identification of cytomegalovirus and the HI- or AIDS-virus.

DETAILED DESCRIPTION OF THE INVENTION

Figure 1:
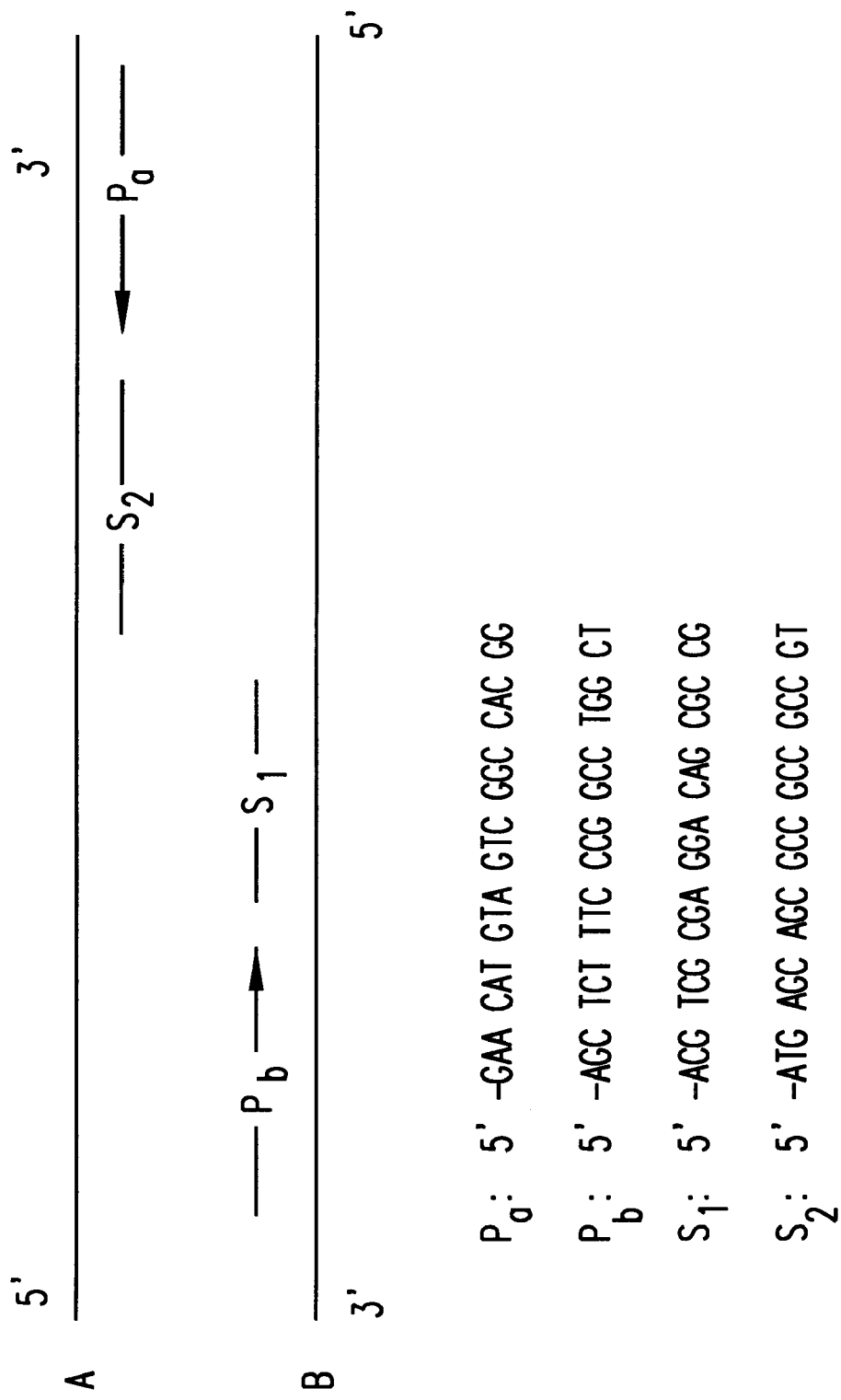
FIG. 1 represents the base sequence of the modified primers, $P_a$ and $P_b$, as well the selective probes, $S_1$ and $S_2$, used in Example 1, 2 and 3, as well as the relative sites of the modified primers, $P_a$ and $P_b$, and the selective probes, $S_1$ and $S_2$, on the target nucleic acid in question. The long lines, A and B, indicate the two target strands which continue in both directions. The arrowheads on the primers, $P_a$ and $P_b$, indicate the direction in which they are elongated in the polymerization process.

Preparation of assay material.

The probes used in the method are oligo- or polynucleotides. The probes can be prepared synthetically or semi-synthetically, which are the preferred mode to prepare probes, which will act as primers, too. It is also quite possible to prepare the probes by recombinant techniques, or from nucleic acids isolated directly from nature. A probe may be bound to a suitable vector. It may contain vector parts or be completely devoid of vector parts. Actually a multitude of suitable primers and probes, which can be used, are commercially available.

The detector probes as modified primers.

In one of the methods of the present invention the detector probes are oligonucleotides or polynucleotides, which can be bound to the target nucleic acid by base-pairing and which can act as primers for a template dependent nucleic acid synthesizing enzyme. It is essential that the detector primers are provided with at lest one suitable, detectable label or at least one specific site whereto at least one suitable detectable label can be attached.

Various radioactive isotopes or radioactively labelled compounds may be used as labels. The label substance may also be fluorescent, luminescent, light emitting, enzymatically or immunologically demonstrable etc. Labels based on the affinity of biotin and avidin or streptavidin, lanthanide chelates, ferritin and heme compounds, and immunologically demonstrable haptens such as AAF and AIF (acetoxyacetylfluorene derivatives) can be mentioned as examples. Identification by the aid of mediators, for example proteins, is also possible.

The method according to the invention is not dependent on the label used. All currently known label substances suitable for nucleic acid hybridization can be freely applied to the method. It is, however, essential that if the detector probes act as primers, the label is selected from a group of labels, which will not disturb the function of the primer. The label has to be attached to the detector primer in such a way that the nucleic acid polymerizing enzyme still can recognize it as a primer.

The capturing probes as primers.

In the other method of the present invention the capturing probes are oligonucleotides or polynucleotides which can be bound to the target nucleic acid by base-pairing and which can act as primers for a template dependent nucleic acid synthesizing enzyme. It is essential that the capturing primers are provided with at least one suitable moiety of an affinity pair or at least one site whereto at least one suitable moiety of an affinity pair can be attached. It is also possible to attach the moiety or moieties of the affinity pair through a mediator to the capturing primer. The only conditions are that it is possible to separate the hybrid from the hybridization solution by the aid of the affinity pair and that the primer function is not harmed.

It is not necessary to attach the moiety or moieties of the affinity pair to the capturing primer at the beginning of the polymerization. It may be added at any time after the polymerization process to the modified primer having been incorporated into the copies of the target nucleic acid.

The moiety of the affinity pair is a component having affinity for another component. For example, biotin—avidin or streptavidin, a heavy metal derivative—a thiogroup, various homopolynucleotides such as poly dG —poly dC, poly dA—poly dT, and poly dA—poly U, are such affinity pairs. But also other component pairs can be used, provided that they have affinity strong enough to allow their specific binding to the affinity column. Suitable affinity pairs are found among ligands and conjugates used in immunological methods.

The selective capturing probe.

In one of the methods of the present invention, wherein the detector probes act as primers, a selective capturing probe is required to allow the selective separation of the modified primers being incorporated into the copies of the target nucleic acids. It is essential that the capturing probes are sufficiently homologous to the target nucleic acid to allow specific hybridization and thereby selective separation of the detector primers having been incorporated into the copies of the target nucleic acid.

The selective detector probe.

In the other method of the present invention, wherein the capturing probes act as modified primers, a selective detector probe is required to allow the detection of the modified primers being incorporated into the copies of the target nucleic acids. It is essential that the detector probe is sufficiently homologous to the target nucleic acid to hybridize specifically and thereby to identify the target nucleic acid selectively. The detector probes can be provided with any suitable, detectable labels for example with those mentioned above.

Reagent combinations.

The detector probe as a modified primer.

The present invention relates to a reagent combination comprising at least one modified primer, provided with at least one suitable, detectable label or at least one specific site whereto at least one suitable, detectable label can be attached and at least one selective capturing probe provided with at least one moiety of an affinity pair or at least one specific site whereto at least one moiety of an affinity pair can be attached.

The capturing probe as a modified primer.

The present invention relates also to a reagent combination comprising at least one modified primer provided with at least one suitable moiety of an affinity pair or at least one specific site whereto at least one suitable moiety of an affinity pair can be attached and at least one selective detector probe provided with at least one suitable, detectable label or at least one specific site whereto at least one suitable, detectable label can be attached.

Kits.

The present invention also discloses a convenient kit for assaying nucleic acids. The kit comprises in packaged form a multicontainer unit in which one of the reagent combinations mentioned above is combined with at least one of the following reactants or facilities needed in the test i.e. optionally a container comprising at least one template dependent polymerization agent, optionally a container with the four deoxynucleoside triphosphates, optionally a suitable facility for the polymerization and the hybridization process, optionally a suitable facility for the separation of the copies of the target nucleic acids and optionally a suitable facility for assaying the label. The preferred facilities and reactants are described in more detail in the following part of the specification.

The method of the invention

The preferred method of the present invention starts by adding at least two modified primers, both primers being either detector or capturing primers, to a denaturated sample solution. The modified primers will each anneal to their complementary strand of the target nucleic acid, i.e. the template and upon addition of a template dependent nucleic acid synthesizing enzyme the primers will be elongated. The process proceeds efficiently in vitro creating new nucleic acid strands which may be several thousand bases in length, provided the conditions are suitable.

By using an excess of modified primers the process may be repeated to create complementary copies to the newly synthesized strands, which thus are identical copies of the first template. By repeating this process a cascade reaction is initiated whereby the target nucleic acid is multiplied. The process may be repeated as many times as desired, to obtain the desired detection sensitivity. In cases where the concentration of target nucleic acid is not extremely low one multiplication is sufficient to make the target nucleic acid detectable.

It is also possible to use only one modified primer in the method of the invention. In this case the multiplication is, however, not so efficient as by using at least two primers because the reaction is not a cascade type reaction.

Both DNA and RNA can be determined by the method of the present invention. However, if the target nucleic acid is RNA it is most convenient first to copy the RNA to the corresponding cDNA by reverse transcriptase enzyme, whereafter the process continues as described above.

After the modified primers are incorporated into the copies of the target nucleic acids, a suitable selective probe recognizing the target sequence and its copies is added to the reaction mixture and the hybridization reaction is performed under conditions suitable for the respective hybridization process chosen.

In the hybridization reaction, depending on the choice of modified primers, either a selective capturing probe or a selective detector probe is allowed to hybridize with the copies of the target nucleic acid now present in multifolded amounts compared to the amount of the target nucleic acid in the original situation.

If the original sample contained the target sequence the added selective probe will hybridize to newly synthetized copies of the target nucleic acid. A hybrid is formed between the modified primer-target molecule and the selective probe. The hybrids formed are according to the present invention, conveniently separated from the hybridization solution by the aid of the moiety of the affinity pair, which is attached, either on the capturing primer or on the selective capturing probe. During fractionation these capturing moiety containing hybrids adhere to a solid carrier by the aid the other moiety of the affinity pair and the amount of selective detector probe or detector primer adhering to the carrier can be measured by conventional methods directly from the carrier or after elution from the eluate. The amount of label is a measure of the amount of target nucleic acid.

Before the fractionation, the solution is diluted, when necessary, to render the conditions advantageous for the affinity pair. Thereafter the solution is contacted with the solid carrier. The carrier in question may be for instance an affinity chromatography column, a filter, a plastic surface or a glass surface. Convenient facilities for performing the separation are different types of microtiter plates, dipstick systems or magnetic particles, but it is quite possible to perform the separation in test tubes and on beads etc.

The carrier material of the affinity column may be for instance, cellulose, latex, polyacrylamide, polystyrene, dextran or agarose. These materials can also be used as suspensions in a test tube. It is also advantageous to use test tubes having the other moiety of an affinity pair fixed to its inner surface. It is a prerequisite for the material selected that it is possible to fix to it a component having affinity to the moiety of the affinity pair which is attached to the capturing primer or the selective capturing probe.

The separation of hybrid by the aid of one moiety of an affinity pair must not necessarily be made using an affinity pair coupled to a solid carrier. Whenever the chemical or physical behaviour of the modified primer-target-selective probe complex differs enough from that of the free detector primer or from the free selective detector probe it can be separated from them for example by using electric or magnetic fields, phase extraction or precipitation.

If the detector probes act as modified primers incorporated into the copies of the target nucleic acid, the hybrid can be separated from the reaction mixture by the aid of selective capturing probes immobilized on solid carriers. In this method the rate limiting step is created when the target nucleic acid and its copies, wherein detector primers have been incorporated, must hybridize with the selective capturing probe that is immobilized on a solid carrier. Therefore, the hybridization in solution is a more preferred method of the invention than this. However, if the method is carried out by using an immobilized capturing probe, the hybrid formed on the solid carrier is washed and the amount of the label on the carrier is measured by conventional methods.

EXAMPLE 1

Detection of cytomegalovirus DNA by using detector probes as modified primers

The principle of the test is demonstrated in Example 1. In this model experiment the target is a recombinant plasmid (pBR322/CMV HindIII L) which harbours a 12.3 kb fragment of the cytomegalovirus (CMV, AD 169, ATCC VR-538) genome. The two detector primers ($P_a$, $P_b$, FIG. 1) used were 20 nucleotides long and synthesized with standard methods on an automated synthesizer. They corresponded to two regions on the CMV-specific insert which were 111 nucleotides apart. Two selective capturing probes ($S_1$, $S_2$, FIG. 1) recognized regions on each of the two strands between the two detector primers. The detector primers Pa and $P_b$, were labelled with $^{32}P$ at their 5' ends to a specific activity of $4 \times 10^9$ CPM/µg using the well known reaction with polynucleotide kinase and gamma-$^{32}$P-ATP (Maniatis et al., Molecular Cloning, A Laboratory Manual, Cold Spring Harbor Laboratory, 1982).

Biotinvlated nucleotides were added to the 3' ends of the capturing probes using bio 11-dUTP and terminal transferase as described by Riley et al., DNA, 5 (4), pp. 333–337, 1986. The target plasmid was linearized by cleavage with the restriction enzyme EcoRI. DNA polymerase, Klenow fragment was purchased from Boenringer-Mannheim and streptavidin agarose from.

Using these reagents the following experiment was performed.

Four different reactions were assembled containing 0, $10^4$, $10^6$ and $10^8$ molecules (corresponding to 0, $2 \times 10^{-20}$, $2 \times 10^{-18}$ and $2 \times 10^{-16}$ moles) respectively of the target plasmid. In addition all four reactions contained in a total volume of 50 µl: 2 pmol each of the two primers, 0, 5 mM of each of the four deoxynucleoside triphosphates (i.e. dATP, dCTP, dGTP and dTTP), 10 mm Tris-Cl pH 7, 5 10 mM MgCl$_2$, 50 mM NaCl and 10 mM dithiothreitol. The mixture was heated to 100° C. for 2 min, then incubated for 5 min at 37° C., whereafter 1 µl (equalling 1 unit) of DNA-polymerase was added. Then the mixture was again incubated for 10 min at 37° C. The boiling followed by annealing of the detector primers and an incubation with added DNA polymerase at 37° C. constitutes a DNA synthesizing cycle.

In this experiment the cycle was either performed only once or repeated 5 or 15 times. After the last cycle the sample was again heated to 100° C. whereafter 10 pmole of the selective capturing probe was added together with NaCl, (0, 9 M) EDTA (20 mM) sodium phosphate pH 7, 5 (20 mM) and sodium dodecyl sulphate (0.1%). The volume increased to 100 μl and the concentrations given are as final concentrations. The mixture was then incubated at 50° C. for 1 h. After this hybridization reaction 200 μl of a 25% suspension of streptavidin-agarose in 1 M NaCl, 20 mM sodium phosphate, pH 7, 5, 1 mM EDTA was added. Biotinylated molecules were allowed to bind to the streptavidin-agarose for 15 min at 37° C. in a rotating mixer. The agarose was collected by brief centrifugation and the supernatant removed by aspiration. The agarose was then washed once in the buffered 1 M NaCl and twice in a solution containing 150 mM NaCl, 15 mM sodium citrate 0.2% sodium dodecyl sulphate (pH 8) at 37° C. The radioactivity of the agarose to which the formed hybrids were bound was then determined in a radioactivity counter. The harvesting and washing procedure for DNA hybrids containing a biotinylated marker are previously known procedures described e.g. in British Patent Publication No. 2 169 403.

The results of the experiment are shown in Table 1. It is seen that one cycle of DNA synthesis incorporates enough radioactivity for detection only if high target concentrations are present, but that even the very low target amount is detectable after 15 cycles. With high amount of target and 15 cycles the amount of detector primer became limiting.

TABLE 1

| Amount of | 32 P-activity in collected hybrids [a] (CPM above background) [b] | | | |
|---|---|---|---|---|
| target (moles) | 1 | 5 | 15 | No. of cycles |
| 0 | 0 | 0 | 0 | |
| $2 \times 10^{-20}$ | ND | ND | 650 | |
| $2 \times 10^{-18}$ | ND | 300 | 11000 | |
| $2 \times 10^{-16}$ | 700 | 13000 | 36000 | |

[a] Mean of two determinations
[b] ND - not detectable (less radioactivity than 2 times mean background activity)

EXAMPLE 2

Determination of cytomegalovirus DNA by using capturing probes as modified primers.

In this example the capturing probes act as primers. The reagents used were the same as in Example 1 with the following exceptions: The capturing primers ($P_a$, $P_b$, FIG. 1) were not labelled with $^{32}P$ but their 5' ends were instead modified to contain a biotin residue. This chemical modification was done using known methods described by Chollet and Kawashima, Nucleic Acids Research, 13, pp. 1529–1541, 1985. The two selective probes ($S_1$ and $S_2$, FIG. 1) were in this case labelled in their 5' ends to act as detector probes. Their specific activities were approximately $2 \times 10^9$ and 2, $5 \times 10^9$ cpm/μg respectively.

The reaction mixtures were assembled as described in Example 1. The biotinylated capturing primers were, however, added in 10 fold amounts, i.e. 20 pmol each per reaction. 1, 5 or 15 cycles were performed as described whereafter the samples were heated to 100° C. and 0, 5 pmol each of the $^{32}P$-labelled probes $S_1$ and $S_2$ were added. The hybridization was carried out in the same conditions as described in Example 1.

The hybrids were then collected on streptavidin-agarose, washed and counted for $^{32}P$-activity, as in Example 1. The result is shown in Table 2.

TABLE 2

| Amount of | $^{32}P$-acitivity in collected hybrids [a] (CPM above background) [b] | | | |
|---|---|---|---|---|
| target (moles) | 1 | 5 | 15 | No. of cycles |
| 0 | 0 | 0 | 0 | |
| $2 \times 10^{-20}$ | ND | ND | 800 | |
| $2 \times 10^{-18}$ | ND | 400 | 13000 | |
| $2 \times 10^{-16}$ | 300 | 11000 | 54000 | |

[a] Mean of two determinations
[b] ND - Not detectable (cf ex 1)

EXAMPLE 3

Detection of cytomegalovirus DNA from clinical samples by using capturing probes as modified primers.

In this example the applicability of the method for the study of clinical samples is demonstrated by detecting CMV from the urine of an infant known to suffer from cytomegalovirus infection. The urine from a healthy child was included as a control. Both samples were 10 ml of urine from which the total DNA was isolated as described in Virtanen et al., J. Clin. Microbiol., 20 (6), pp. 1083–1088, 1984. The DNAS, dissolved into 20 μl $H_2O$ were used as target in reactions which otherwise were performed as described in Example 2. After 10 cycles of DNA-synthesis the labelled selective probe was added to the sample, allowed to hybridize, and the hybrids collected. The DNA from the urine of the patient showed a clearly elevated radioactivity in hybrids while that from the healthy person showed background radioactivity only. The actual cpm-values were 2300 and 240 respectively.

EXAMPLE 4

Detection of Semiliki Forest virus RNA by using capturing probes as modified primers.

Example 4 is to demonstrate that the method described also can be used for the detection of RNA. The model used was the RNA from Semliki Forest virus (SFV).

Figure 2:
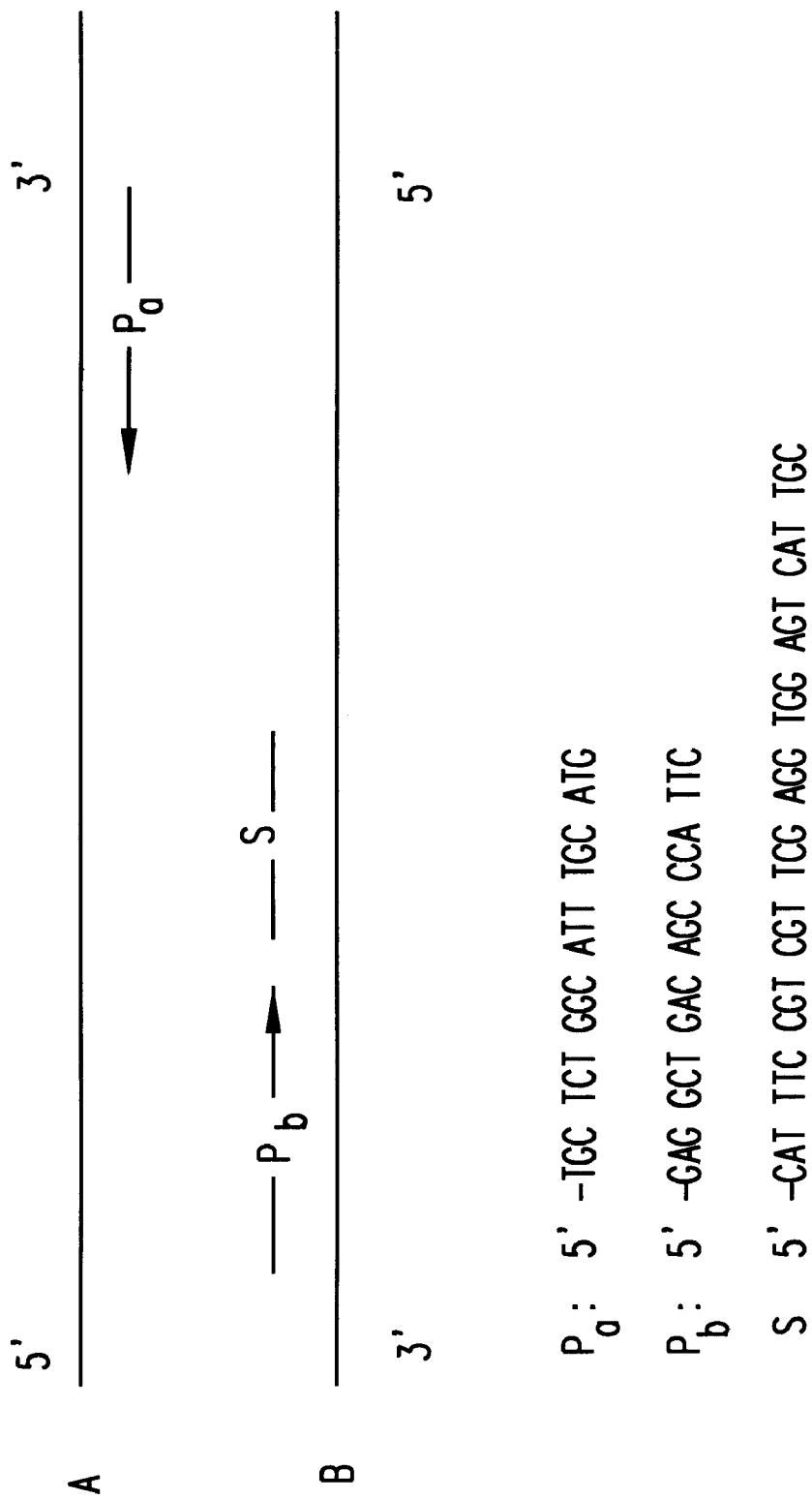
FIG. 2 represents the base sequence of the modified primers, $P_a$ and $P_b$, and the selective probe, S used in Example 4, as well as the relative sites of the modified primers, $P_a$ and $P_b$ and the selective probe S on the target nucleic acid in question. Line A indicates the RNA and its identical DNA copies and line B shows the complementary DNA copies. The arrowheads on the primers $P_a$ and $P_b$ indicate the direction in which they are elongated in the polymerization process.

The reagents used were two 5' biotinylated capturing primers (FIG. 2) (prepared as described in Example 2), a single 5' $^{32}P$-labelled selective detector probe (prepared as described in Example 1), reverse transcriptase (Promega Biotech, and DNA polymerase, Klenow fragment (Boehringer Mannheim).

The first step in the detection of the SFV-RNA was to synthesize a cDNA copy. The 20 μl reaction mixture contained 10 mM tris-Cl pH 8.3, 50 mM KCl, 10 mM $MgCl_2$, 10 mM dithiothreitol 0, 5 mm each of the four deoxynucleoside triphosphates, 0, 5 μg t-RNA, 10 pg of SFV-RNA, 10 pmol of capturing primer $P_a$ and 100 U reverse transcriptase. This mixture was incubated at 37° C. for 15 min. Then the mixture was heated to 100° C. for 5 min and cooled to ambient temperature. Thereafter 50 μl of a solution containing 10 mM Tris-Cl pH 7, 4, 50 mM NaCl, 10 mM $MgCl_2$, 10 mM dithiothreitol, 10 pmol of the capturing primer $P_b$ and 0, 5 mM of each of the 4 deoxynucleosidetriphosphates. The temperature was elevated to 37° C. and after 5 min 1 U of DNA-polymerase was added. After an additional 10 min incubation the reaction mixture was incubated at 100° C. for 5 min, the mixture was cooled to 37° C. and 5 cycles of DNA synthesis was performed. After a final denaturation step 0.1 pmol (1, $2 \times 10^6$ cpm) of the selective detector probe was added in 80 μl M NaCl, 50 mM EDTA, 50 mM sodium-phosphate (pH 7, 5) 0.1% sodium dodecyl sulphate. The solution was then incubated for 2 h at 55° C. whereafter the hybrids were collected and washed as described in Example 1.

As a negative control for the reactions an identical sample was given the same treatment except for that no reverse transriptase was added. The sample in which the RNA was converted to cDNA with reverse transcriptase yielded 420 cpm $^{32}$P-activity in captured hybrids, while the negative control yielded 50 cpm.

What is claimed is:

1. A method for assaying for a target nucleic acid comprising the steps of
   (a) providing to a sample which comprises a target nucleic acid a capturing primer, in which the capturing primer comprises at least one moiety of an affinity pair or at least one specific site to which at least one moiety of an affinity pair can be attached;
   (b) exposing said capturing primer to the target nucleic acid, in single-stranded form, under conditions wherein a template dependent polymerization reaction occurs, and a complementary copy of the single-stranded target nucleic acid is formed which comprises the capturing primer;
   (c) exposing the complementary copy of the single-stranded target nucleic acid to a detector probe having a sequence which selectively hybridizes to the complementary copy of the single-stranded target nucleic acid, under conditions wherein a hybridization reaction occurs;
   (d) binding the capturing primer comprised in the complementary copy of the single-stranded target nucleic acid to a retrievable form of the other moiety of the affinity pair;
   (e) separating the complementary copy of the single-stranded target nucleic acid hybridized to the detector probe from the remainder of the sample by retrieving the bound affinity pair; and
   (f) detecting the presence of the hybridized nucleic acids with the aid of the detector probe.

2. The method as claimed in claim 1, wherein the target nucleic acid comprises a first strand and a second strand, and two capturing primers are provided according to step (a), in which one of said capturing primers hybridizes to the first strand of the target nucleic acid and the other capturing primer hybridizes to the second strand of the target nucleic acid.

3. The method as claimed in claim 1, wherein at least one moiety of an affinity pair is attached to the capturing primer after the polymerization reaction of step (b) but before binding the capturing primer of step (d).

4. A method according to claim 1, wherein the target nucleic acid is cytomegalovirus DNA.

5. A method according to claim 1, wherein the target nucleic acid is Semliki forest virus DNA.

6. A method for assaying for a double-stranded target nucleic acid comprising the steps of
   (a) providing to a sample comprising a double-stranded target nucleic acid a plurality of capturing primers, in which the capturing primers each comprise at least one moiety of an affinity pair or at least one specific site to which at least one moiety of an affinity pair can be attached;
   (b) denaturing the double-stranded target nucleic acid;
   (c) exposing said capturing primers to the target nucleic acid, in single-stranded form, under conditions wherein a template dependent polymerization reaction occurs, whereby complementary copies of the single-stranded target nucleic acid are formed which comprise the capturing primers;
   (d) exposing the complementary copies of the single-stranded target nucleic acid to a plurality of detector probes, each detector probe having a sequence which selectively hybridizes to a complementary copy of the single-stranded target nucleic acid, under conditions wherein a hybridization reaction occurs;
   (e) binding the capturing primers comprised in the complementary copies of the single-stranded target nucleic acid to a plurality of the other moiety of the affinity pair in retrievable form;
   (f) separating the complementary copies of the single-stranded target nucleic acid hybridized to the detector probes from the remainder of the sample by retrieving the bound affinity pairs; and
   (g) detecting the presence of the hybridized nucleic acids with the aid of the detector probes.

7. A method for assaying for a double-stranded target nucleic acid comprising the steps of
   (a) providing to a sample comprising a double-stranded target nucleic acid a plurality of capturing primers, in which the capturing primers each comprise at least one moiety of an affinity pair or at least one specific site to which at least one moiety of an affinity air can be attached;
   (b) denaturing the double-stranded target nucleic acid;
   (c) exposing said capturing primers to the target nucleic acid, in single-stranded form, under conditions wherein a template dependent polymerization reaction occurs, whereby a complementary copy of the single-stranded target nucleic acid is formed which comprises a capturing primer;
   (d) denaturing the complementary copy from the single-stranded target nucleic acid;
   (e) repeating steps (b) and (c) until a plurality of complementary copies of the single-stranded target nucleic acid have been produced;
   (f) exposing the complementary copies of the single-stranded target nucleic acid to a plurality of detector probes, each detector probe having a sequence which selectively hybridizing to a complementary copy of the single-stranded target nucleic acid, under conditions wherein a hybridization reaction occurs;
   (g) binding the capturing primers comprised in the complementary copies of the single-stranded target nucleic acid to a plurality of the other moiety of the affinity pair in retrievable form;
   (h) separating the complementary copies of the single-stranded target nucleic acid hybridized to the detector probes from the remainder of the sample by retrieving the bound affinity pairs; and
   (i) detecting the presence of the hybridized nucleic acids with the aid of the detector probes.

8. The method as claimed in claim 6, in which some capturing primers bind to one strand of the target nucleic acid and other capturing primers bind to the other strand of the target nucleic acid.

9. The method as claimed in claim 7, in which some capturing primers bind to one strand of the target nucleic acid and other capturing primers bind to the other strand of the target nucleic acid.

* * * * *